US010743765B2

(12) United States Patent
Sun

(10) Patent No.: US 10,743,765 B2
(45) Date of Patent: Aug. 18, 2020

(54) MINIATURE IMAGING SYSTEM FOR OPHTHALMIC LASER BEAM DELIVERY SYSTEM

(71) Applicant: AMO Development, LLC, Santa Ana, CA (US)

(72) Inventor: Zheng Sun, Milpitas, CA (US)

(73) Assignee: AMO Development, LLC, Santa Ana, CA (US)

( * ) Notice: Subject to any disclaimer, the term of this patent is extended or adjusted under 35 U.S.C. 154(b) by 329 days.

(21) Appl. No.: 15/788,530

(22) Filed: Oct. 19, 2017

(65) Prior Publication Data
US 2019/0117065 A1 Apr. 25, 2019

(51) Int. Cl.
*A61B 3/14* (2006.01)
*G02B 27/10* (2006.01)
(Continued)

(52) U.S. Cl.
CPC .......... *A61B 3/14* (2013.01); *G02B 5/04* (2013.01); *G02B 17/045* (2013.01); *G02B 17/08* (2013.01);
(Continued)

(58) Field of Classification Search
CPC . A61B 3/14; G02B 5/04; G02B 17/04; G02B 17/045; G02B 17/08–0896; G02B 23/02; G02B 27/108; G02B 27/14
(Continued)

(56) References Cited

U.S. PATENT DOCUMENTS 4,834,526 A * 5/1989 Nunokawa ............... A61B 3/14
351/206
5,163,437 A * 11/1992 Fujii ................... A61B 3/1233
600/476
(Continued)

FOREIGN PATENT DOCUMENTS

CN 101248981 A 8/2008
EP 2581060 A1 4/2013
(Continued)

OTHER PUBLICATIONS

Anonymous: "Bauernfeind Prism", Wikipedia, the free Encyclopedia, Jan. 13, 2018, XP002787719, Retrieved from the Internet: URL:https://en.wikipedia.org/wiki/bauernfeind_prism [retrieved on Jan. 1, 2019].
(Continued)

*Primary Examiner* — Kristina M Deherrera
(74) *Attorney, Agent, or Firm* — Johnson & Johnson Surgical Vision, Inc.

(57) ABSTRACT

An optical imaging system for an ophthalmic laser beam delivery system, which includes a focusing objective including a plurality of lenses, a semi-transparent folding mirror disposed near an entrance of the focusing objective for reflecting a treatment laser beam into the focusing objective, a prism disposed adjacent a back surface of the folding mirror, the prism having a first, a second and a third surface, the second surface being disposed adjacent the back surface of the folding mirror, the prism being configured to reflect a light that has entered the second surface sequentially by the first surface and by the second surface toward the third surface to be output, a focusing lens module disposed adjacent the third surface of the prism to focus light output from the third surface of the prism, and an image sensor
(Continued)

disposed to receive the light focused by the focusing lens module to form an image.

14 Claims, 5 Drawing Sheets

(51) Int. Cl.
    *G02B 17/04*     (2006.01)
    *G02B 23/02*     (2006.01)
    *G02B 5/04*     (2006.01)
    *G02B 17/08*     (2006.01)
    *G02B 27/14*     (2006.01)
    *A61B 18/22*     (2006.01)
    *A61F 9/008*     (2006.01)

(52) U.S. Cl.
    CPC ........... *G02B 23/02* (2013.01); *G02B 27/108* (2013.01); *G02B 27/14* (2013.01); *A61B 2018/2261* (2013.01); *A61F 9/008* (2013.01); *A61F 2009/00897* (2013.01)

(58) Field of Classification Search
    USPC ........ 351/205, 206, 221, 246, 215; 606/4–6; 359/529–533, 831
    See application file for complete search history.

(56) References Cited

U.S. PATENT DOCUMENTS

| | | |
|---|---|---|
| 5,949,583 A | 9/1999 | Rallison et al. |
| 7,158,293 B2 | 1/2007 | Hund et al. |
| 8,366,271 B2 | 2/2013 | Izatt et al. |
| 2008/0002152 A1 | 1/2008 | Collins et al. |
| 2009/0250828 A1 | 10/2009 | Rosen et al. |
| 2015/0216408 A1* | 8/2015 | Brown ................. A61B 3/1015 351/206 |
| 2015/0272782 A1 | 10/2015 | Schuele et al. |
| 2016/0161731 A1 | 6/2016 | Brueck et al. |
| 2016/0360960 A1 | 12/2016 | Angeley et al. |

FOREIGN PATENT DOCUMENTS

| | | |
|---|---|---|
| EP | 2111785 B1 | 12/2014 |
| GB | 2433608 A | 6/2007 |
| JP | 2015215618 A | 12/2015 |

OTHER PUBLICATIONS

International Search Report and Written Opinion for Application No. PCT/US20181056523, dated Feb. 20, 2019, 16 pages.

\* cited by examiner $$\left(\frac{TD}{\cos\left(\frac{n_1\sin(b_1-dAng)}{n_2}\right)}-\frac{TD}{\cos\left(\frac{n_1\sin(b_1)}{n_2}\right)}\right)$$

$$=\frac{L_1\sin(y_1)}{\cos\left(y_1-\mathrm{asin}\left(\frac{20\sin(a_1)}{31}\right)\right)}-\frac{\sin(y_2)(L_1-L+\frac{L_1\sin(2y_1-2\mathrm{asin}(\frac{20\sin(a_1)}{31}))\sin(y_1)}{\cos(y_1-\mathrm{asin}(\frac{20\sin(a_1)}{31}))\cos(2y_1-\mathrm{asin}(\frac{20\sin(a_1)}{31})+\frac{1}{2})}}{\sin(2y_1-y_2-\mathrm{asin}(\frac{20\sin(a_1)}{31}))}$$

$$\frac{\sin(y_1)(L_1-dL)}{\cos\left(y_1-\mathrm{asin}\left(\frac{20\sin(a_1-\frac{\pi}{36})}{31}\right)\right)}-\frac{\sin(y_2)(L-L_1+dL-\frac{\sin(2y_1-2\mathrm{asin}(\frac{20\sin(a_1-\frac{\pi}{36})}{31}))\sin(y_1)(L_1-dL)}{\cos(y_1-\mathrm{asin}(\frac{20\sin(a_1-\frac{\pi}{36})}{31}))\cos(2y_1-2\mathrm{asin}(\frac{20\sin(a_1-\frac{\pi}{36})}{31})+\frac{1}{2})}}{\sin(2y_1-y_2-\mathrm{asin}(\frac{20\sin(a_1-\frac{\pi}{36})}{31}))}$$

$$=\frac{L_1\cos(2y_1-2\mathrm{asin}(\frac{20\sin(a_1)}{31}))\sin(y_1)}{\cos(y_1-\mathrm{asin}(\frac{20\sin(a_1)}{31}))}+\frac{\cos(2y_1-2\mathrm{asin}(\frac{20\sin(a_1-\frac{\pi}{36})}{31}))\sin(y_1)(L_1-dL)}{\cos(y_1-\mathrm{asin}(\frac{20\sin(a_1-\frac{\pi}{36})}{31}))}$$

$$+\frac{L_1\sin(2y_1-2\mathrm{asin}(\frac{20\sin(a_1)}{31}))\tan(2y_1-\mathrm{asin}(\frac{20\sin(a_1)}{31}))}{\cos(y_1-\mathrm{asin}(\frac{20\sin(a_1)}{31}))}=\frac{\sin(2y_1-2\mathrm{asin}(\frac{20\sin(a_1-\frac{\pi}{36})}{31}))\tan(2y_1-\mathrm{asin}(\frac{20\sin(a_1-\frac{\pi}{36})}{31}))\sin(y_1)(L_1-dL)}{\cos(y_1-\mathrm{asin}(\frac{20\sin(a_1-\frac{\pi}{36})}{31}))}$$

Fig. 4

MINIATURE IMAGING SYSTEM FOR OPHTHALMIC LASER BEAM DELIVERY SYSTEM

BACKGROUND OF THE INVENTION

Field of the Invention

This invention relates to an optical imaging system, and in particular, it relates to a miniature optical imaging system for an ophthalmic laser beam delivery system.

Description of Related Art

In a laser system for ophthalmic surgery, the laser beam from a laser device (the treatment laser beam) is delivered by a laser beam delivery optical system to the patient's eye to treat the eye. A part of the beam delivery system is located in a delivery head of the laser system, which is moveably mounted on a mounting structure and is brought to the proximity of the eye for performing the treatment. Typically, an optical imaging system is provided for the beam delivery system to capture light from the eye. The light from the eye may be, for example, light backscattered, reflected, or refracted from the eye, or otherwise generated by the eye under illumination by an illumination light or in response to the treatment laser beam, such as fluorescence, Raman scatter, bremsstrahlung from plasma formation, etc. The captured light forms an image of the eye, which can be used in a variety of ways to assist in preparing for or performing the surgery, such as docking the delivery head to the eye (i.e. the process of mechanically coupling the delivery head to the patient's eye via a patient interface device), range finding (i.e. determining the depths of various structural components of the eye), etc.

FIG. 1 schematically illustrates a conventional laser beam delivery system incorporating an imaging system. In the orientation of FIG. 1, the patient lies on his/her back and the beam delivery head 20 is located above the eye. The delivery head 20 includes a focusing objective 22 including a series of lenses arranged vertically to focus the treatment beam 30 to desired locations of the eye. The delivery head 20 also includes a folding mirror 24 located at the entrance of the focusing objective 22 (i.e. above the series of lenses) and disposed at an angle (e.g. a 45-degree angle) with respect to the optical axis of the focusing objective to reflect the treatment beam 30 into the focusing objective. The delivery head 20 additionally includes a beam splitter 26 located at the exit of the focusing objective (i.e. below the lenses) to reflect a part of the light from the eye away from the optical axis of the focusing objective; additional light guiding optics, such as a Bauernfeind prism, are provided to guide that light (the imaging signal) to an imaging sensor 28.

The imaging sensor 28 is located on the side and near the lower end of the focusing objective 22. The beam splitter 26, the light guiding optics, and the imaging sensor 28 are mounted within an imaging module housing 29, which is rotatable around the optical axis of the focusing objective 22. To accommodate the sensor 28, the light guiding optics, and other structures inside of it, the imaging module housing 29 extends laterally and occupies a space near a lower end and on one side of the focusing objective 22 (the first side, to the right of the focusing objective in the configuration shown in FIG. 1); on the opposite side of the focusing objective (the second side, to the left of the focusing objective in the configuration shown in FIG. 1), the imaging module housing 29 extends laterally only by a minimum amount. During treatment, the lowest end 29a of the imaging module housing 29 is engaged with the patient's eye via a patient interface device, and the free space near the lowest end 29a on the second side of the focusing objective 22 can accommodate the patient's nose bridge. When treating the other eye, the imaging module housing 29 needs to be rotated around the optical axis of the focusing objective 22 by about 180 degrees, so as to accommodate the nose bridge which is now on the other side of the eye being treated.

SUMMARY

One disadvantage of the configuration shown in FIG. 1 is that the imaging module housing 29 is bulky, and due to its location right above the lowest point 29a of the delivery head, blocks the surgeon's view of the eye and limits the freedom to manipulate the patient interface device during docking.

Accordingly, the present invention is directed to an imaging system for an ophthalmic laser beam delivery system that substantially obviates one or more of the problems due to limitations and disadvantages of the related art.

An object of the present invention is to provide an imaging system for an ophthalmic laser beam delivery system while minimizing the space occupied by the imaging system near the lower end of the beam delivery head.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an optical imaging system for an ophthalmic laser beam delivery system, which includes: a focusing objective including a plurality of lenses; a folding mirror disposed near an entrance of the focusing objective for reflecting a treatment laser beam into the focusing objective, wherein the folding mirror reflects a part and transmits a part of the light incident on it; a prism disposed adjacent a back surface of the folding mirror that faces away from the focusing objective, the prism having a first, a second and a third surface, the second surface being disposed adjacent the back surface of the folding mirror, the prism being configured to reflect a light that has entered the second surface sequentially by the first surface and by the second surface toward the third surface to be output; a focusing lens module disposed adjacent the third surface of the prism to focus light output from the third surface of the prism; and an image sensor disposed to receive the light focused by the focusing lens module to form an image.

It is to be understood that both the foregoing general description and the following detailed description are exemplary and explanatory and are intended to provide further explanation of the invention as claimed.

BRIEF DESCRIPTION OF THE DRAWINGS

FIG. 4 shows a mathematical equation used to calculate the parameters of the prism according to an embodiment of the present invention.

DETAILED DESCRIPTION OF PREFERRED EMBODIMENTS

Figure 1:
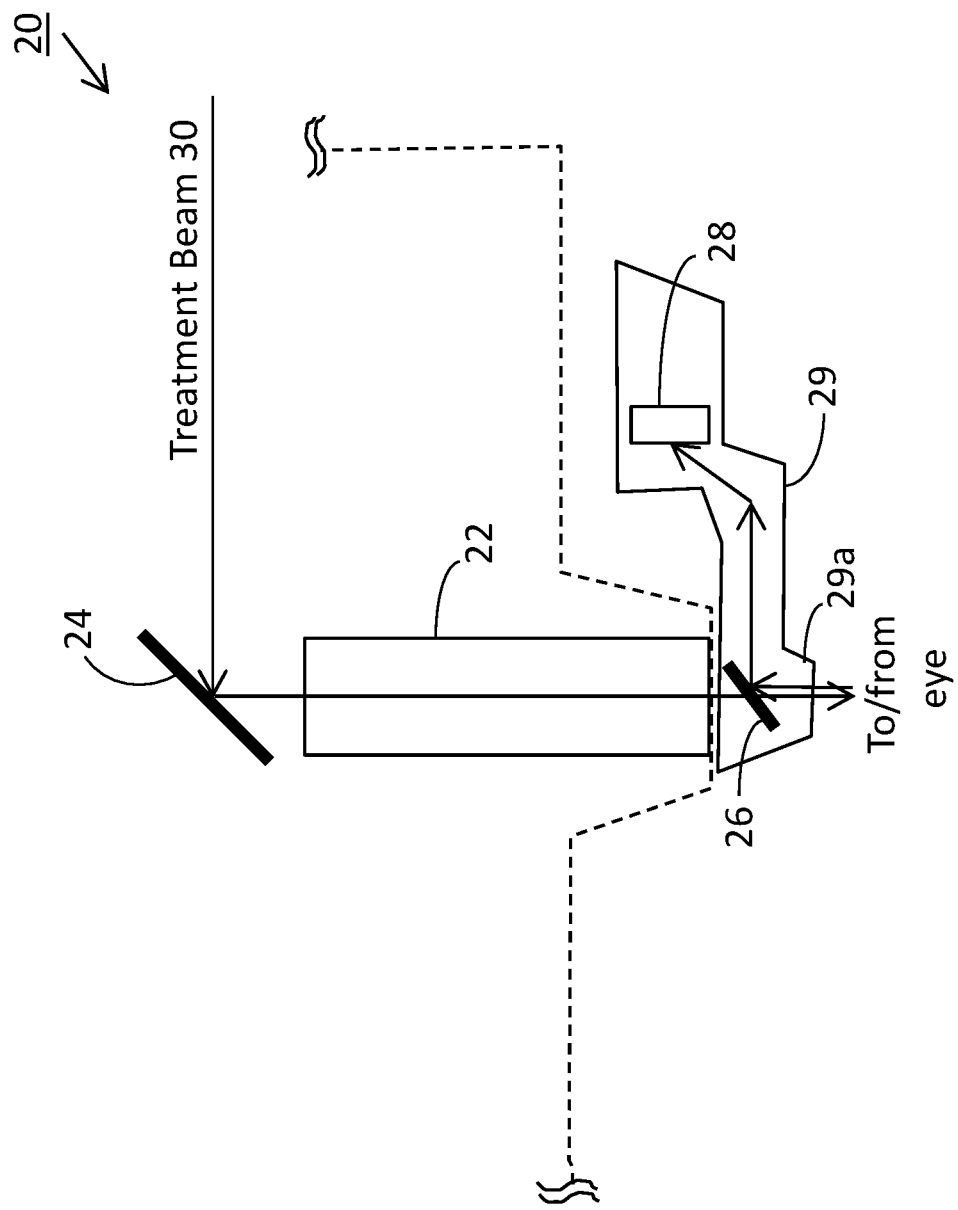
FIG. 1 schematically illustrates a part of a conventional laser beam delivery head for an ophthalmic laser system.

According to an embodiment of the present invention, the conventional beam delivery system shown in FIG. 1 is modified by providing an imaging sensor and related optics on the back side of the folding mirror 24/14, i.e. the mirror that reflects the treatment beam 30 to the entrance of the focusing objective 22. Thus, some structures shown in FIG. 1, including the beam splitter 26 located at the exit of the focusing objective 22 and the imaging sensor 28 located in the imaging module housing 29, can be eliminated; as a result, the housing 29 can be significantly reduced in size, or eliminated, so that on both sides of the focusing objective there is sufficient free space to accommodate the patient's nose bridge. Therefore, a rotatable housing is not necessary, and the surgeon will have much improved visibility of the patient's eye and room to manipulate the patient interface during docking.

Figure 2A:
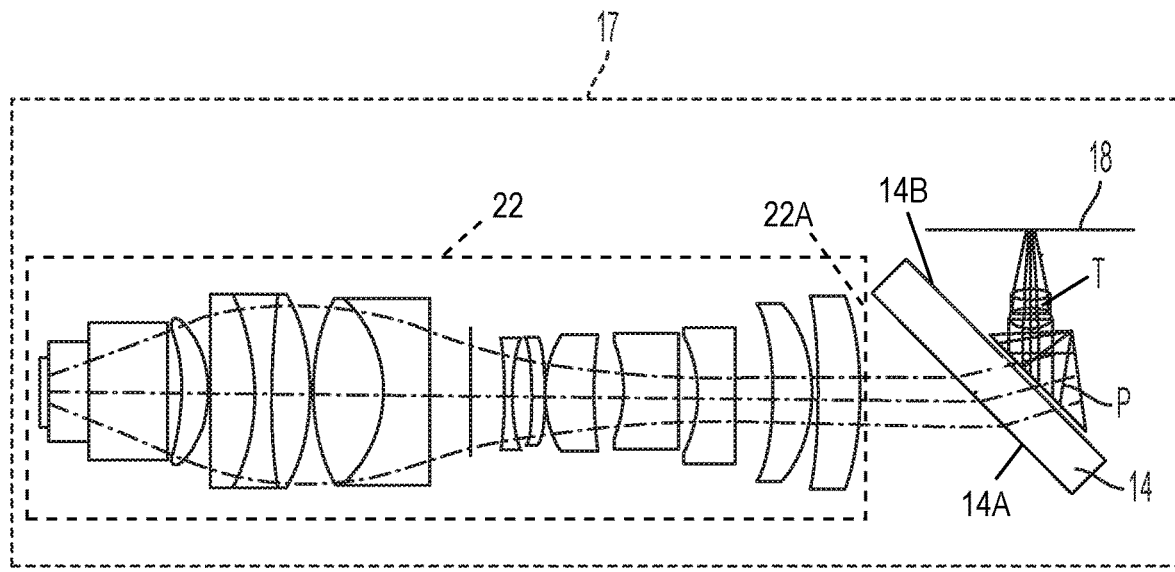
FIGS. 2A to 2D schematically illustrate a miniature imaging system in a laser beam delivery head for an ophthalmic laser system according to an embodiment of the present invention.
Figure 2B:
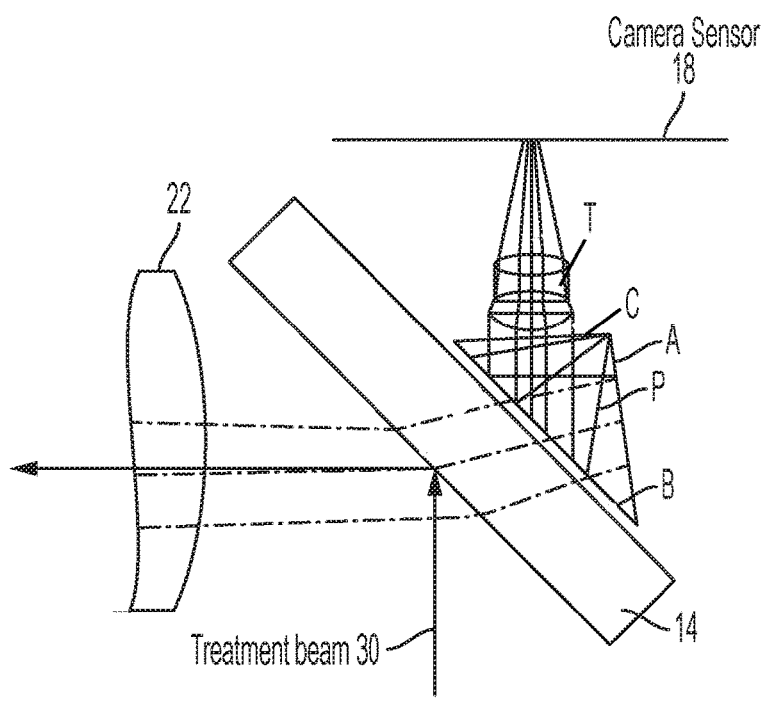

FIGS. 2A and 2B schematically illustrates the structure of the imaging system according to an embodiment of the present invention. FIG. 2A shows the imaging system in relation to the focusing objective; FIG. 2B is an enlarged view of the imaging system. Note that the orientation of FIGS. 2A and 2B is rotated clockwise by 90 degrees from that of FIG. 1.

The focusing objective 22 includes a series of lenses; the folding mirror 14 is located at the entrance 22A of the focusing objective 22 to reflect the incoming treatment laser beam 30 (which is incident on the front surface 14A of the folding mirror, which faces the focusing objective) into the focusing objective. The folding mirror 14 is a semi-transparent mirror which reflects a part and transmits a part of the light incident on it. A prism P is disposed behind the folding mirror 14, i.e., on the side facing away from the treatment laser beam and the focusing objective (i.e. the back side). The prism P is preferably made of glass, and has three surfaces, with the second surface B being approximately parallel to and disposed in close proximity to the back surface 14B of the folding mirror 14. The structure of the prism P will be described in more detail later.

The light from the eye is collected by the objective 22, and a part of the collected light passes through the folding mirror 14. This light enters the prism P form the second surface B and strikes the first surface A of the prism P. The light is reflected by the first surface A, which is coated with a reflective coating, and strikes the second surface B again, where it is reflected by total internal reflection. The light reflected by the second surface B passes through the third surface C to exit the prism P. The light is then focused by a focusing lens module T, which may include, for example, a Cooke triplet lens, to form an image on the imaging sensor 18. The input surface of the sensor 18 is preferably parallel to the optical axis of the focusing objective 22 and perpendicular to the incoming treatment beam 30.

Figure 2D:
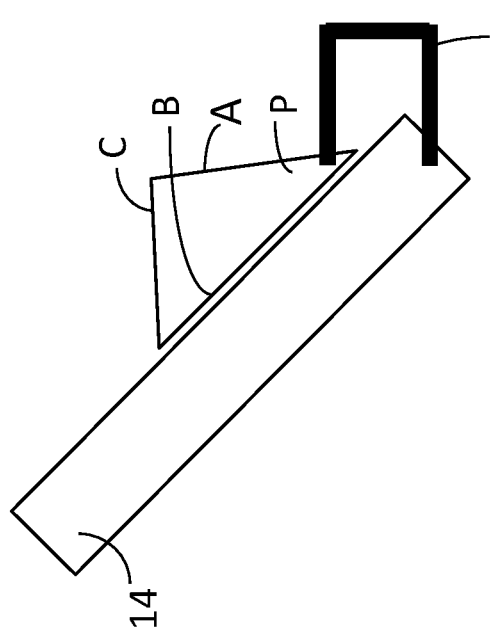
Figure 2C:
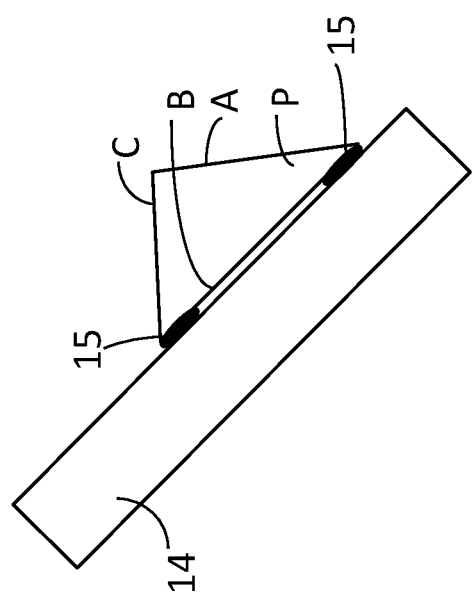

The prism P may be attached to the back surface of the folding mirror 14 by an adhesive 15 (see FIG. 2C), preferably one having a similar refractive index as that of the prism (e.g. a refractive-index matching glue). Alternatively, a mechanical mounting structure 16 may be used to mount the prism P in the required spatial relationship with respect to the folding mirror 14 (see FIG. 2D). The mechanical mounting structure is not shown in the drawings, but any suitable structure may be used, such as clamps, brackets, etc., and those skilled in the relevant art will be able to construct such a mounting structure without undue experimentation. When a mechanical mounting structure is used, the second surface B of the prism P is preferably spaced apart from the back surface of the folding mirror 14 by a thin gap which may be filled with air or another optical medium. Because sometimes the angle of the second surface B of the prism relative to the back surface of the folding mirror 14 may need to be adjusted (e.g., to an angle up to 20 degrees), a thin gap facilitates such adjustment. In one embodiment, the thickness of the gap is a few mm.

The image sensor 18 may employ any suitable sensor. In one embodiment, the image sensor 18 has a size of approximately 6 mm by 6 mm and a spatial resolution of 200 pixels/mm.

The focusing objective 22, the folding mirror 14, the prism P, the focusing lens T and the image sensor 18 are fixedly mounted with respect to each other in the same housing 17 (see FIG. 2A) and moved together during normal operation of the laser beam delivery system.

As seen from FIG. 1 and FIG. 2A, in the preferred embodiment, the folding mirror 14 is located directly above the focusing objective 22, at approximately the same location of the folding mirror 24 shown in FIG. 1; the image sensor 18 is located at approximately the same vertical height of the folding mirror 14 and to one side of the optical axis of the objective 22, i.e. the side opposite to the incoming treatment laser beam; the light from the eye, after being collected by the focusing objective 22 and passing though the folding mirror 14, is reflected by the prism P to travel in a substantially horizontal direction before reaching the image sensor 18. Compared to the conventional structure shown in FIG. 1, where the image sensor 28 is physically located in a space near the lower end of the focusing objective 22 and at a relatively small distance above the lowest end 29a of the beam delivery head, in the preferred embodiment of FIG. 2A, the image sensor 18 is located at a relatively high location of the beam delivery head, and the housing 29 can be eliminated or substantially reduced in size, so that it will not interfere with the surgeon's visibility and manipulation of the patient interface device.

Moreover, by using the triangular prism P, the physical distance between the folding mirror 14 and the image sensor 18 can be short while providing a required optical path length for focusing. This is accomplished by using a glass material which has a relatively high refractive index for the prism P, and by reflecting the light through the three-segmented path within the prism as described above.

Further, aberrations introduced by the folding mirror 14, which has two parallel surfaces, may be corrected by designing the angles of the triangular prism P. A triangular prism introduces aberration itself, which is often considered a disadvantage. In the optical design of the present embodiment, however, the aberration introduced by the prism P can be used to compensate for the aberration introduced by the folding mirror 14 through the design of the angles of the prism.

Thus, the parameters of the triangular prism P, including its angles and size, as well as its position relative to the folding mirror, can be designed to achieve the above described functions and goals. The following method may be used to calculate the preferred parameters of the prism P and its placement relative to the folding mirror.

Figure 3:
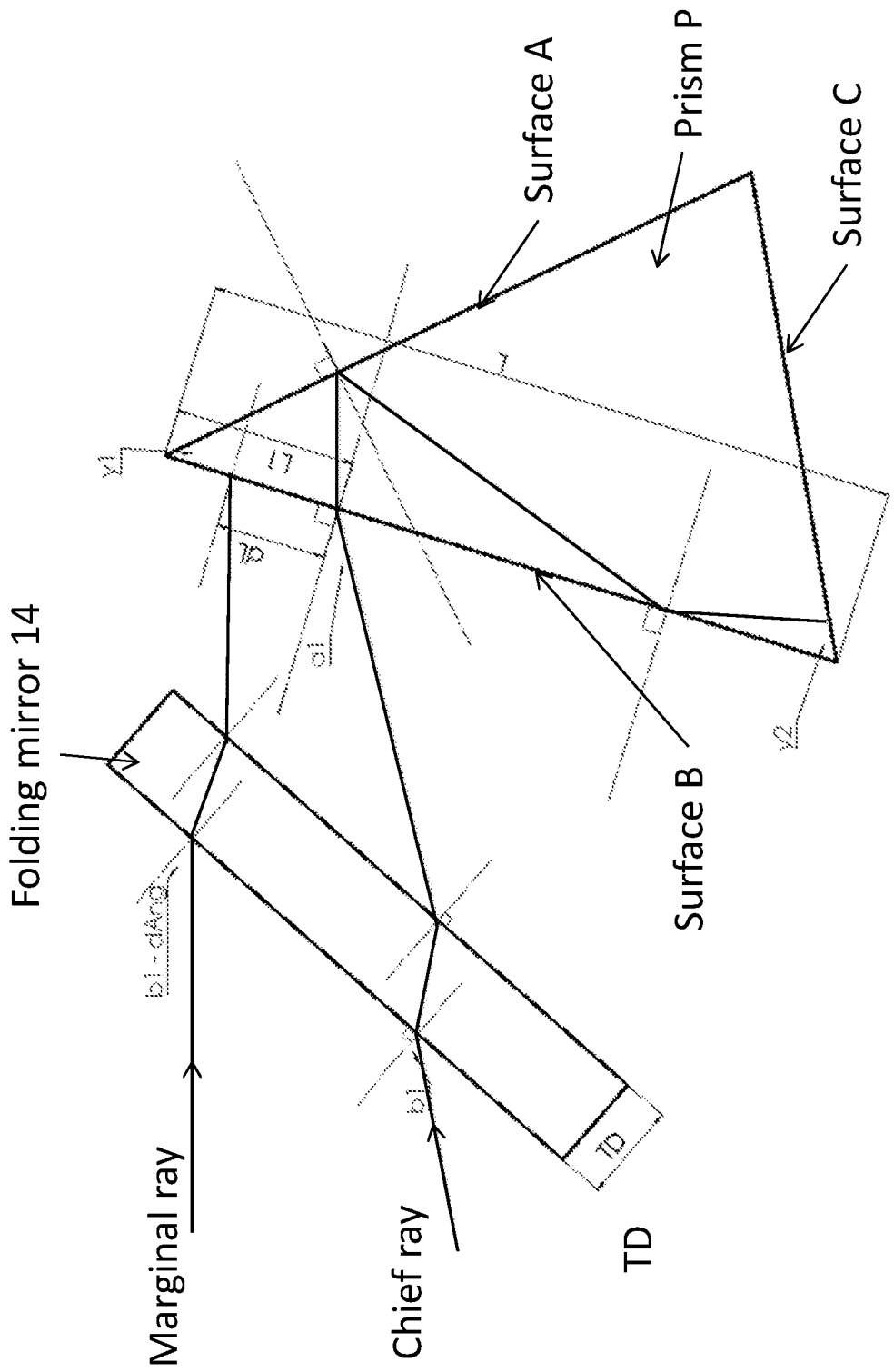
FIG. 3 schematically illustrates a folding mirror, a prism, and the optical paths of light rays traveling through these optical components, in a model used to calculate the parameters of the prism according to an embodiment of the present invention.

FIG. 3 schematically illustrates the folding mirror 14, the prism P, and the optical paths of marginal and chief ray from the focusing objective 22 and traveling through these optical components. The chief ray is a light ray traveling along the center of the focusing objective 22 and parallel to its optical axis. The marginal ray is a light ray located at an edge of the light cone from the focusing objective 22. The incident angles of the chief ray and the marginal ray on the folding mirror are respectively b1 and b1−dAng, where dAng is one half of the convergence angle of the converging light cone that exits the focusing objective and enters the folding mirror. After passing through the folding mirror, the chief ray strikes surface B of the prism at an incident angle a1 and at a location that is at a distance L1 from the edge of the prism formed by surface A and surface B. The marginal ray strikes surface B at an incident angle a1−dAng and at a location that is at a distance L1−dL from the same edge. FIG. 3 depicts the path of the chief ray as it travels from surface B to surface A, reflected by surface A which have reflective coating back to surface B, reflected by surface B by total internal reflection, and exits surface C. The path of the marginal ray is not depicted in FIG. 3.

To achieve aberration compensation, the optical paths of the chief ray and the marginal ray should be equal. An equation (Equation 1) with universal conditions that achieves this aberration compensation is shown in FIG. 4. In Equation 1 (also referring to FIG. 3), y1 is the angle between surface B and surface A, y2 is the angle between surface B and surface C, L is the length of surface B, TD is the thickness of the folding mirror, n2 is the refractive index of the folding mirror and the prism (for example, they may be made of the same material), and n1 is the refractive index of the optical medium on both sides of the folding mirror. From Equation 1, it can be seen that the various parameters of the prism P and the folding mirror can be adjusted to achieve the aberration compensation.

The parameters b1, dAng, n1, n2, and TD are determined by the system's optical components upstream of the prism P, including the focusing objective 22 and the folding mirror 14. Once these parameter are given, Equation 1 can be simplified. If surface B of the prism is parallel to the back surface of the folding mirror (i.e. a1=b1), Equation 1 can be further simplified. The simplified equation will give the relationship between the prism's parameters that will achieve aberration compensation.

For example, in one particular example,
b1=45 degrees (i.e., the folding mirror 14 is at a 45-degree angle with respect to the optical axis of the focusing objective 22);
dAng=10 degrees (i.e., the convergence angle of the focus light cone from the focusing objective 22 is 20 degrees);
n1=1 (air);
n2=1.46;
TD=8 mm;
dL=5 mm
L=20 mm;
a1=b1 (i.e., surface B of the prism is parallel to the back surface of the folding mirror); and
y1=30 degrees.

Using these conditions, the following simplified equation (Equation 2) can be derived from Equation 1:

$$L1 = \frac{\frac{30.0 \sin(y_2)}{\sin(1.073 - 1.0 y_2)} - \frac{35.59 \sin(y_2)}{\sin(1.12 - 1.0 y_2)} + 5.583}{\frac{1.059 \sin(y_2)}{\sin(1.073 - 1.0 y_2)} - \frac{1.118 \sin(y_2)}{\sin(1.12 - 1.0 y_2)} + 0.03279}$$

Thus, when the above parameters are fixed, aberration compensation can be achieved by adjusting y2 (the angle between surface B and surface C) and L1 (the placement of the prism relative to the folding mirror) according to Equation 2. For example, if y2=45 degrees, then from Equation 2, L1=14.74 mm will achieve the desired aberration compensation result. Equation 2 also means that when the prism size and angles are fixed, the prism can be slid along the direction parallel to the folding mirror.

By designing the parameters of the prism P and its placement relative to the folding mirror in the manner described above, an aberration compensation effect can be achieves, for example, the combined aberration of the folding mirror and the prism can be less than 10% of the aberration of the mirror itself.

In a preferred embodiment, the angle between the first surface A and second surface B of the prism between 40 and 20 degrees, and the angle between the third surface C and second surface B is between 40 and 50 degrees.

Those skilled in the art would appreciate that the corners between the three surfaces may be truncated without affecting the function of the prism.

Advantages of the imaging system of the present embodiment include: (1) The imaging module which include the prism P, the focusing lens T and the imaging sensor 18 can be made physically small, and can be mounted at the back side of the folding mirror 14. (2) The imaging module is light weight, and can be mounted with the moving part of the beam delivery system. (3) The prism P is mounted as close as possible to the entrance of the focusing objective without impacting the treatment beam delivery, which can increase the image signal intensity and provide sufficient spatial frequency information.

It will be apparent to those skilled in the art that various modification and variations can be made in the imaging system and related method of the present invention without departing from the spirit or scope of the invention. Thus, it is intended that the present invention cover modifications and variations that come within the scope of the appended claims and their equivalents.

What is claimed is:
1. An optical imaging system for an ophthalmic laser beam delivery system, comprising:
a focusing objective including a plurality of lenses;
a folding mirror disposed near an entrance of the focusing objective, wherein the folding mirror has a front surface that faces the entrance of the focusing objective and a back surface that faces away from the entrance of the focusing objective, wherein the folding mirror is configured to reflect a part of a treatment laser beam that is incident on the front surface into the entrance of the focusing objective, wherein the folding mirror is further configured to transmit a part of a collected light, which has exited the entrance of the focusing objective and incident on the front surface, out of the back surface;
a prism disposed adjacent the back surface of the folding mirror, the prism having a first, a second and a third surface, the second surface being disposed adjacent the back surface of the folding mirror and configured to receive the part of the collected light that has exited the entrance of the focusing objective and transmitted through the folding mirror out of the back surface of the folding mirror, the prism being configured to reflect the part of the collected light that has entered the second surface sequentially by the first surface and by the second surface toward the third surface to exit the prism;

a focusing lens module disposed adjacent the third surface of the prism to focus light exiting from the third surface of the prism, the focusing lens module being distinct from the focusing objective; and an image sensor disposed to receive the light focused by the focusing lens module to form an image.

2. The optical imaging system of claim 1, wherein the prism is made of glass.

3. The optical imaging system of claim 1, wherein the second surface of the prism is substantially parallel to the back surface of the folding mirror.

4. The optical imaging system of claim 1, wherein the first surface of the prism is coated with a reflective coating, and wherein the second surface of the prism reflects light from the first surface toward the third surface by total internal reflection.

5. The optical imaging system of claim 1, wherein an angle between the first surface and the second surface of the prism is between 20 and 40 degrees, and an angle between the third surface and the second surface of the prism is between 40 and 50 degrees.

6. The optical imaging system of claim 1, wherein the folding mirror and the prism have identical indices of refraction.

7. The optical imaging system of claim 1, wherein the folding mirror generates an aberration when the part of the collected light passes through it, and wherein the prism is configured to generate an aberration when the part of the collected light enters the second surface, is sequentially reflected by the first surface and the second surface, and exits the third surface, and wherein a combined aberration of the folding mirror and the prism is less than 10% of the aberration generated by the folding mirror.

8. The optical imaging system of claim 1, wherein the prism is attached to the back surface of the folding mirror by an adhesive.

9. The optical imaging system of claim 1, wherein the prism is mounted adjacent to the back surface of the folding mirror by a mechanical mounting structure.

10. The optical imaging system of claim 9, wherein the second surface of the prism is spaced apart from the back surface of the folding mirror by a gap.

11. The optical imaging system of claim 10, wherein the gap is filled with air.

12. The optical imaging system of claim 1, wherein the focusing lens module includes a Cooke triplet lens.

13. The optical imaging system of claim 1, wherein a receiving surface of the image sensor is parallel to an optical axis of the focusing objective.

14. The optical imaging system of claim 1, wherein the focusing objective, the folding mirror, the prism, the focusing lens module and the image sensor are fixedly mounted with respect to each other in a housing.

* * * * *